United States Patent
Wei et al.

(10) Patent No.: US 11,065,617 B2
(45) Date of Patent: Jul. 20, 2021

(54) FLOW PASSAGE DESIGN FOR MULTI-REACTION BIOLOGICAL DETECTION AND DETECTION METHOD THEREOF

(71) Applicant: SKYLA CORPORATION HSINCHU SCIENCE PARK BRANCH, Hsinchu (TW)

(72) Inventors: Chia-Chun Wei, Taipei (TW); Hung-Wei Chen, Taipei (TW); Ping-Hsing Ho, Taipei (TW)

(73) Assignee: SKYLA CORPORATION HSINCHU SCIENCE PARK BRANCH, Hsinchu (TW)

( * ) Notice: Subject to any disclaimer, the term of this patent is extended or adjusted under 35 U.S.C. 154(b) by 180 days.

(21) Appl. No.: 15/641,208

(22) Filed: Jul. 3, 2017

(65) Prior Publication Data
US 2018/0304256 A1  Oct. 25, 2018

(30) Foreign Application Priority Data
Apr. 19, 2017  (CN) .......................... 201710256394.0

(51) Int. Cl.
*B01L 3/00* (2006.01)
*G01N 33/49* (2006.01)

(52) U.S. Cl.
CPC ..... *B01L 3/502715* (2013.01); *B01L 3/50273* (2013.01); *B01L 3/502746* (2013.01);
(Continued)

(58) Field of Classification Search
CPC ....... B01L 2200/0621; B01L 2300/087; B01L 2400/0409; B01L 3/50273;
(Continued)

(56) References Cited

U.S. PATENT DOCUMENTS

| | | | |
|---|---|---|---|
| 2001/0055812 A1 | 12/2001 | Mian et al. | |
| 2004/0089616 A1* | 5/2004 | Kellogg .............. | B01F 13/0059 210/749 |
| 2007/0125942 A1* | 6/2007 | Kido ................... | B01F 13/0059 250/284 |

FOREIGN PATENT DOCUMENTS

| | | |
|---|---|---|
| EP | 1462805 | 9/2004 |
| JP | 2002512783 | 5/2002 |

(Continued)

OTHER PUBLICATIONS

Office Action of Japan Counterpart Application, dated Aug. 30, 2018, pp. 1-5.

(Continued)

*Primary Examiner* — Lyle Alexander
*Assistant Examiner* — Bryan Kilpatrick
(74) *Attorney, Agent, or Firm* — JCIPRNET

(57) ABSTRACT

A flow passage design for multi-reaction biological detection includes a first temporary tank, a second temporary tank, a first microchannel, and a second microchannel. The first temporary tank is configured to temporarily store a first liquid in an initial state. The second temporary tank is configured to temporarily store a second liquid in the initial state. The first microchannel is located upstream of the first temporary tank. The first microchannel has an outlet end and an inlet end, respectively connecting to the first temporary tank and the second temporary tank. The second microchannel is located downstream of the first temporary tank and connects to the first temporary tank. In the initial state, a portion of the first liquid enters the second microchannel, the outlet end of the first microchannel is covered by the first liquid, and the inlet end of the first microchannel is covered by the second liquid.

9 Claims, 7 Drawing Sheets

(52) U.S. Cl.
CPC ...... *G01N 33/49* (2013.01); *B01L 2200/0605* (2013.01); *B01L 2200/0621* (2013.01); *B01L 2200/10* (2013.01); *B01L 2200/16* (2013.01); *B01L 2300/0803* (2013.01); *B01L 2300/087* (2013.01); *B01L 2300/0883* (2013.01); *B01L 2400/0406* (2013.01); *B01L 2400/0409* (2013.01)

(58) Field of Classification Search
CPC ....... B01L 2300/0867; B01L 3/502753; B01L 2200/0605; B01L 2200/10; B01L 2200/16; B01L 2400/0406; G01N 1/38; G01N 33/4875
See application file for complete search history.

(56) References Cited

FOREIGN PATENT DOCUMENTS

| | | |
|---|---|---|
| JP | 2015515263 | 5/2015 |
| WO | 2006070772 | 7/2006 |
| WO | 2008106782 | 9/2008 |
| WO | 2016161402 | 10/2016 |
| WO | 2017013561 | 1/2017 |

OTHER PUBLICATIONS

"Office Action of Taiwan Counterpart Application", dated Aug. 6, 2018, p. 1-p. 6.
"Search Report of Europe Counterpart Application", dated Jan. 23, 2018, p. 1-p. 8.

\* cited by examiner

FLOW PASSAGE DESIGN FOR MULTI-REACTION BIOLOGICAL DETECTION AND DETECTION METHOD THEREOF

CROSS REFERENCE TO RELATED APPLICATION

This application claims the priority benefit of China application serial no. 201710256394.0, filed on Apr. 19, 2017. The entirety of the above-mentioned patent application is hereby incorporated by reference herein and made a part of specification.

BACKGROUND OF THE INVENTION

1. Field of the Invention

The invention relates to a flow passage design and a detection method of the flow passage design and particularly relates to a flow passage design for multi-reaction biological detection and a detection method of the flow passage design for multi-reaction biological detection.

2. Description of Related Art

In a conventional process of multi-reaction biological detection, a specimen that is to be detected (such as blood) is required to react with two or more kinds of reagents in sequence before a required detection item is detected from a result of reaction. Besides, in addition to two or more kinds of the reagents that are required, a reaction tank needs to be washed with a cleaning solution and a redundant waste solution needs to be discharged from the reaction tank before reaction with the next reagent. For example, a biological specimen reacts with a first reagent in the reaction tank, and the remaining biological specimen that is not used in a reaction is drained after the reaction is complete. Next, the cleaning liquid is poured into the reaction tank for washing, and the cleaning reagent is drained to ensure no specimen that is not used in the reaction is left in the reaction tank. Lastly, a second reagent is poured into the reaction tank for reaction, and the result of reaction is detected with a detection apparatus.

In order to pour various liquids into the reaction tank in sequence and discharge the waste liquids from the reaction tank before the next liquid is poured into the reaction tank, in general, many tanks and microchannels are required in the conventional flow passage design for multi-reaction biological detection. However, in addition to making the entire structure of the flow passage design excessively complicated, the design of so many tanks and microchannels also poses challenges against the attempt to reduce the volume of the flow passage design, increases difficulties in the manufacturing, and leads to a rise in costs. Therefore, how to effectively simplify the flow passage design for multi-reaction biological detection remains to be an issue.

SUMMARY OF THE INVENTION

The invention provides a flow passage design for multi-reaction biological detection and a detection method of a flow passage design for multi-reaction biological detection capable of significantly reducing the usage of a microchannel as well as the volume.

A flow passage design for multi-reaction biological detection according to an embodiment of the invention includes a first temporary tank, a second temporary tank, a first microchannel, and a second microchannel. The first temporary tank is configured to temporarily store a first liquid in an initial state. The second temporary tank is configured to temporarily store a second liquid in the initial state. A first microchannel is located upstream of the first temporary tank. The first microchannel has an outlet end and an inlet end respectively connecting to the first temporary tank and the second temporary tank. The second microchannel is located downstream of the first temporary tank and connecting to the first temporary tank. In the initial state, a portion of the first liquid enters the second microchannel. In the initial state, the outlet end of the first microchannel is covered by the first liquid, and the inlet end of the first microchannel is covered by the second liquid.

According to an embodiment of the invention, in the initial state, the second liquid is unable to enter the first microchannel.

According to an embodiment of the invention, after the initial state, the flow passage design is rotated for a first time, so the first liquid leaves the first temporary tank through the second microchannel, while the second liquid remains located in the second temporary tank.

According to an embodiment of the invention, after being rotated for the first time, the flow passage design is kept standing for a period, so a portion of the second liquid enters the first microchannel. The flow passage design is then rotated for a second time, so the second liquid leaves the second temporary tank through the first microchannel and enters the first temporary tank.

According to an embodiment of the invention, the flow passage design further includes a reaction tank. The first liquid and the second liquid enter the reaction tank in sequence at different time points.

According to an embodiment of the invention, each of the first liquid and the second liquid is one of a specimen, a reagent and a cleaning liquid.

An embodiment of the invention provides a detection method of the flow passage design for multi-reaction biological detection. The flow passage design at least includes a first temporary tank, a second temporary tank, a first microchannel located upstream of the first temporary tank, and a second microchannel located downstream of the first temporary tank. The detection method includes the following steps: in an initial state, a first liquid is temporarily stored in the first temporary tank, and a second liquid is temporarily stored in the second temporary tank. The first microchannel has an outlet end and an inlet end, respectively connecting to the first temporary tank and the second temporary tank. In the initial state, the outlet end of the first microchannel is covered by the first liquid, the inlet end of the first microchannel is covered by the second liquid, and a portion of the first liquid enters the second microchannel. The flow passage design is rotated for a first time, so the first liquid leaves the first temporary tank through the second microchannel, while the second liquid remains located in the second temporary tank.

According to an embodiment of the invention, in the initial state, the second liquid is unable to enter the first microchannel.

According to an embodiment of the invention, the detection method further includes: keeping the flow passage design standing for a period, so a portion of the second liquid enters the first microchannel; and rotating the flow passage design for a second time, so the second liquid leaves the second temporary tank through the first microchannel and enters the first temporary tank.

According to an embodiment of the invention, the flow passage design further includes a reaction tank, and the first liquid and the second liquid enter the reaction tank at different time points.

Based on the above, in the flow passage design for multi-reaction biological detection and the detection method of a flow passage design for multi-reaction biological detection, the inlet end and the outlet end of the microchannel disposed between the temporary tanks are covered by the liquids stored temporarily in the temporary tanks in the initial state to prevent a capillary phenomenon from being induced and consequently control the timing of the liquids leaving the reaction tank. Through the design, the flow passage design according to the embodiments of the invention is able to admit samples stepwise and significantly reduce the usage of the microchannel, thereby reducing the volume and simplifying manufacturing.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
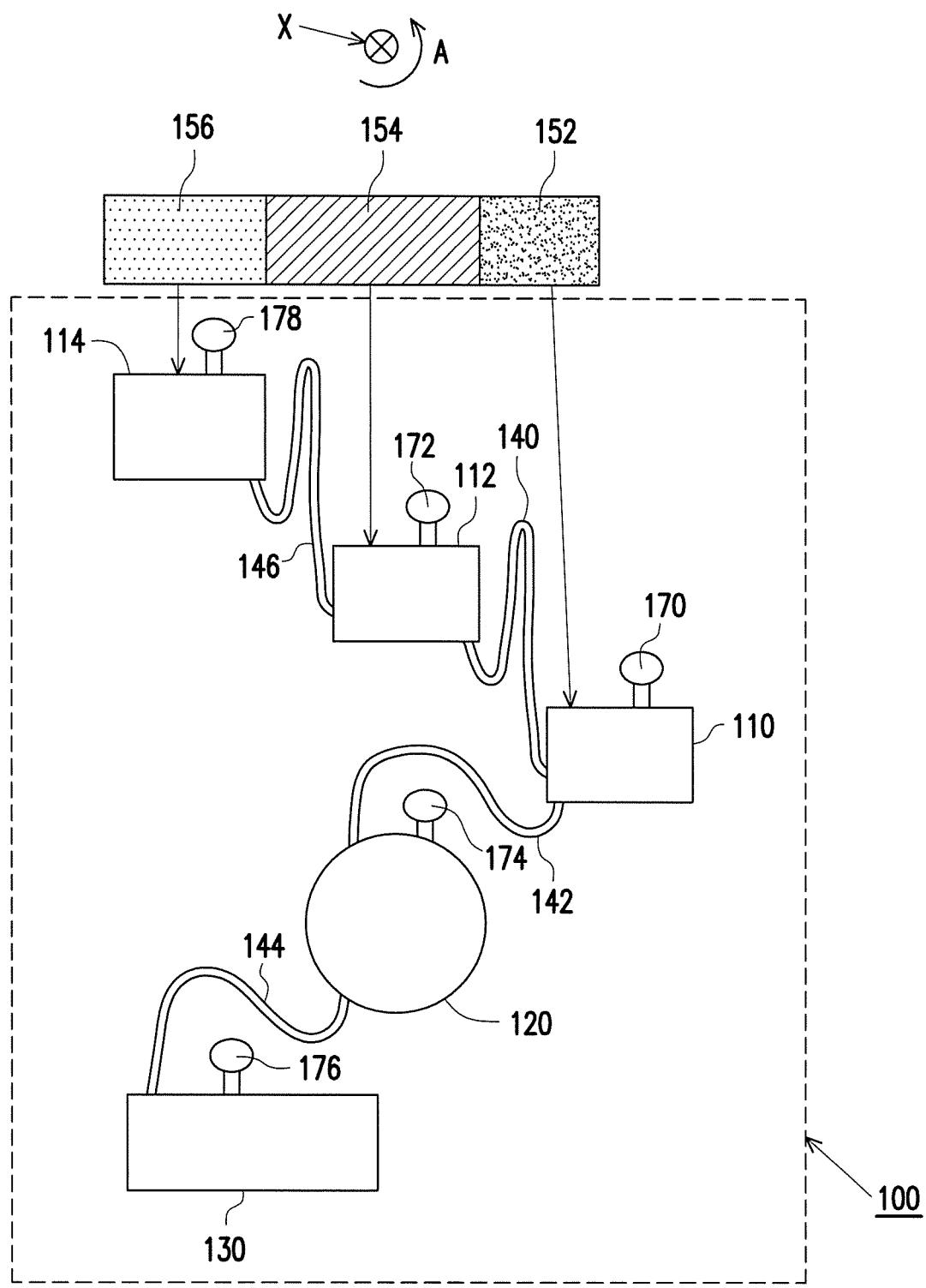
FIG. 1 is a schematic view illustrating a flow passage design for multi-reaction biological detection according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

In the embodiments of the invention, multi-reaction biological detection is defined as a biological detection where a specimen for the biological detection is required to react with at least two kinds of reagents in sequence. In other words, for the multi-reaction biological detection, two or more kinds of liquids are required to be poured into a reaction tank to achieve the multi-reaction biological detection. The liquid may be a specimen, a reagent, a cleaning liquid or such like. The actual kind of the liquids and the sequence of pouring the liquids into the reaction tank may depend on the multi-reaction process of actual biological detection. For instance, in some biological detections, the specimen needs to react with a first reagent in the reaction tank firstly. Next, a cleaning liquid needs to be poured into the reaction tank and is drained together with the remaining specimen that is not used in the reaction. Lastly, a second reagent is poured into the reaction tank to react with a chemical compound in the reaction tank, so the result of reaction is detected with a detection apparatus.

In order to achieve the multi-reaction biological detection in limited volume, the embodiments of the invention provide a flow passage design for multi-reaction biological detection able to effectively reduce the complexity of the flow passage design and lower the difficulty of manufacturing.

For the ease of description, the embodiment of the invention illustrates an example of pouring three kinds of liquids into the reaction tank sequentially. However, in practice, based on the number of the liquids required to be poured into the reaction tank, persons skilled in the art may adjust the number of temporary tanks correspondingly within the framework of the embodiments of the invention.

Referring to FIG. 1, a schematic view of a flow passage design 100 for multi-reaction biological detection according to an embodiment of the invention is illustrated. The flow passage design 100 of the embodiment includes a reaction tank 120, a waste liquid tank 130 and a plurality of temporary tanks 110, 112 and 114. The reaction tank 120, the waste liquid tank 130 and the temporary tanks 110, 112 and 114 are connected by microchannel. The waste liquid tank 130 is located downstream of the reaction tank 120, while the temporary tanks 110, 112 and 114 are located upstream of the reaction tank 120 and sequentially connected in series along a flowing direction of the liquids.

In the embodiment of the invention, based on the number of the liquids that are required to be poured into the reaction tank, the number of the temporary tanks may be equal to or more than the number of the liquids that are required to be poured into the reaction tank to temporarily store the liquids that are required to be poured into the reaction tank respectively in an initial state. In the embodiment, taking liquids 152, 154 and 156 for instance, the number of the temporary tanks may be equal to or more than three. Taking three temporary tanks for instance, the temporary tanks includes the first temporary tank 110, the second temporary tank 112 and the third temporary tank 114 that are configured to temporarily store the three liquids 152, 154 and 156 respectively in an initial state, as FIG. 2A suggests.

Specifically, along the flowing direction of the liquids, the third temporary tank 114 connects to the second temporary tank 112 via a fourth microchannel 146, the second temporary tank 112 connects to the first temporary tank 110 via a first microchannel 140, the first temporary tank 110 connects to the reaction tank 120 via the second microchannel 142, and the reaction tank 120 connects to the waste liquid tank 130 via a third microchannel 144.

Furthermore, the flow passage design 100 of the embodiment may further include a plurality of vents 170, 172, 174, 176 and 178, respectively connecting to the first temporary tank 110, the second temporary tank 112, the reaction tank 120, the waste liquid tank 130 and the third temporary tank 114, so the first temporary tank 110, the second temporary tank 112, the reaction tank 120, the waste liquid tank 130 and the third temporary tank 114 are connected to the outside.

Figure 2A:
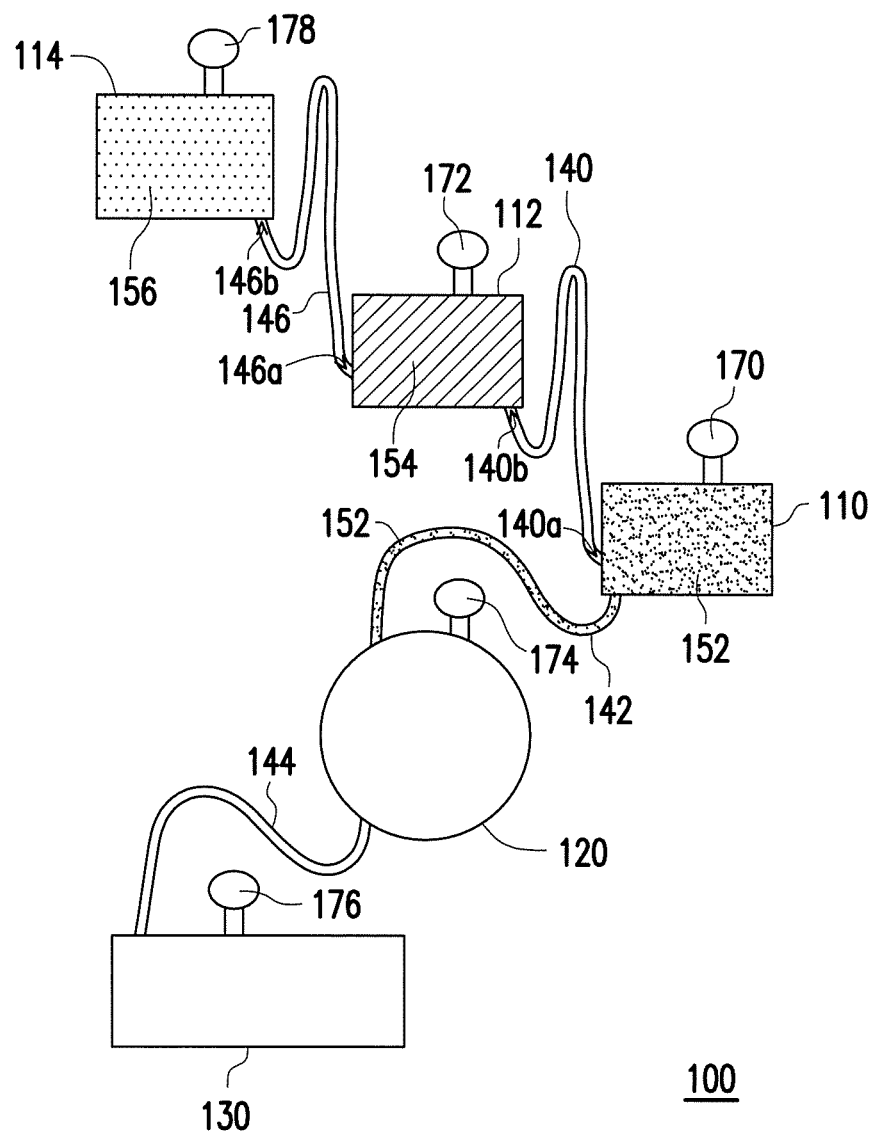
FIGS. 2A to 2F are schematic views illustrating a detection method according to the flow passage design of FIG. 1.

FIGS. 2A to 2F are schematic views illustrating the detection method according to the flow passage design 100 of FIG. 1. Referring to FIG. 2A, FIG. 2A illustrates a schematic view illustrating the initial state of the flow passage design 100 of FIG. 1 in which detection is about to begin. In the initial state, the three liquids 152, 154 and 156 are temporarily stored in the corresponding temporary tanks 110, 112 and 114 according to a sequence of the liquids being poured into the reaction tank 120 and a sequence in which the temporary tanks 110, 112 and 114 are disposed along the flowing direction of the liquids. Specifically, assuming that the three liquids 152, 154 and 156 are the specimen 152, the cleaning liquid 154 and the reagent 156 respectively, and the specimen 152 is firstly poured into the reaction tank 120, followed by the cleaning liquid 154, and then followed by the reagent 156, the specimen 152 is temporarily stored in the first temporary tank 110, and the cleaning liquid 154 and the reagent 156 that are poured subsequently are respectively temporarily stored in the second temporary tank 112 and the third temporary tank 114 sequentially along an upstream direction from the first temporary tank 110.

In the embodiment of the invention, in the initial state, the temporary tanks for storing the liquids temporarily are connected to each other in sequence. In other words, in the initial state, there is no empty temporary tank between the temporary tanks for storing the liquids temporarily. As FIG. 2A suggests, in the initial state, the first temporary tank 110, the second temporary tank 112 and the third temporary tank 114 temporarily storing the specimen 152, the cleaning liquid 154 and the reagent 156 respectively are connected to each other in sequence, and there is no empty temporary tank between the first temporary tank 110, the second temporary tank 112 and the third temporary tank 114. It is noteworthy that the embodiments of the invention do not intend to limit on how the liquids that are to be poured into the reaction tank enter and are stored temporarily in the temporary tanks. The liquids may be provided in the temporary tanks in advance, or collected from the outside and put into the temporary tanks. Alternatively, the liquids may also enter the temporary tanks through other storage tanks other than those of the flow passage design of the embodiments of the invention.

Furthermore, in the embodiment of the invention, the microchannel disposed between the two adjacent temporary tanks of the temporary tanks has an inlet end and an outlet end, respectively connecting to the temporary tank located upstream and the temporary tank located downstream. Taking the first microchannel 140 disposed between the temporary tank 110 and the second temporary tank 112 for example, the first microchannel 140 has an outlet end 140a and an inlet end 140b. The outlet end 140b is connected to the first temporary tank 110 located downstream, while the inlet end 140b is connected to the second temporary tank 112 located upstream. Taking the fourth microchannel 146 disposed between the second temporary tank 112 and the third temporary tank 114 for example, the fourth microchannel 146 has an outlet end 146a and an inlet end 146b. The outlet end 146a is connected to the second temporary tank 112 located downstream, while the inlet end 146b is connected to the third temporary tank 114 located upstream.

In the embodiment of the invention, in the initial state, the inlet end and the outlet end of the microchannel disposed between the two adjacent temporary tanks of the temporary tanks are covered by the liquids in the temporary tanks that are connected to the inlet end and the outlet end. As FIG. 2A suggests, the outlet end 140a and the inlet end 140b of the first microchannel 140 disposed between the first temporary tank 110 and the second temporary tank 112 are covered by the specimen 152 in the first temporary tank 110 and the cleaning liquid 154 in the second temporary tank 112 respectively. The outlet end 146a and the inlet end 146b of the fourth microchannel 146 disposed between the second temporary tank 112 and the third temporary tank 114 are covered by the cleaning liquid 154 in the second temporary tank 112 and the reagent 156 in the third temporary tank 114 respectively.

In the flow passage design illustrated in the embodiments of the invention, the liquid in each tank is driven to flow due to the capillary phenomenon and the siphon phenomenon. Specifically, in the flow passage design according to the embodiments of the invention, the liquid in the tank is driven into the microchannel due to the capillary phenomenon when the flow passage design is kept standing. Then, an external force is applied to the liquid, so the liquid in the microchannel is driven to the next tank due to the siphon phenomenon.

In an embodiment, the flow passage design illustrated in the embodiment of the invention may be rotated to apply a centrifugal force to the liquid as above mentioned external force, and the siphon phenomenon is induced in the liquid in the microchannel. As FIG. 1 suggests, a rotating axis X may be adopted as a center of rotation of the flow passage design 100, and the flow passage design 100 may be rotated along a rotating direction A to generate a centrifugal force to the liquid in the flow passage design 100.

The following is an example of applying the centrifugal force as the external force, detailing the process of the detection method of the flow passage design 100 according to the embodiments of the invention.

Referring to FIG. 2A, in the initial state, the specimen 152, the cleaning liquid 154 and the reagent 156 that are to be sequentially poured into the reaction tank 120 are temporarily stored in the first temporary tank 110, the second temporary tank 112 and the third temporary tank 114 respectively. The inlet end 140b, 146b and the outlet end 140a, 146a of the first microchannel 140 and the fourth microchannel 146 disposed between the first temporary tank 110, the second temporary tank 112 and the third temporary tank 114 are respectively covered by the specimen 152 in the first temporary tank 110, the cleaning liquid 154 in the second temporary tank 112 or the reagent 156 in the third temporary tank 114.

In the initial state, the flow passage design 100 is kept standing for a period. During the period, a portion of the specimen 152 temporarily stored in the first temporary tank 110 enters the second microchannel 142 due to the capillary phenomenon. In addition, since the inlet end 140b and the outlet end 140a of the first microchannel 140 are covered by the cleaning liquid 154 and the specimen 152 respectively, the cleaning liquid 154 is unable to enter the first microchannel 140 by the capillary phenomenon. For the same reason, since the inlet end 146b and the outlet end 146a of the fourth microchannel 146 are covered by the reagent 156 and the cleaning liquid 154 respectively, the reagent 156 is unable to enter the fourth microchannel 146 by the capillary phenomenon.

Next, the flow passage design 100 is rotated to apply a centrifugal force to the liquid in the microchannel. When the flow passage design 100 as shown in FIG. 2A rotated, the specimen 152 in the second microchannel 142 is subjected to the centrifugal force and the siphon phenomenon is induced to drive the specimen 152 in the first temporary tank 110 to enter the reaction tank 120. Besides, since no liquid is in the first microchannel 140 and the fourth microchannel 146, the cleaning liquid 154 in the second temporary tank 112 and the reagent 156 in the third temporary tank 114 are not driven when the flow passage design 100 is rotated.

Figure 2B:
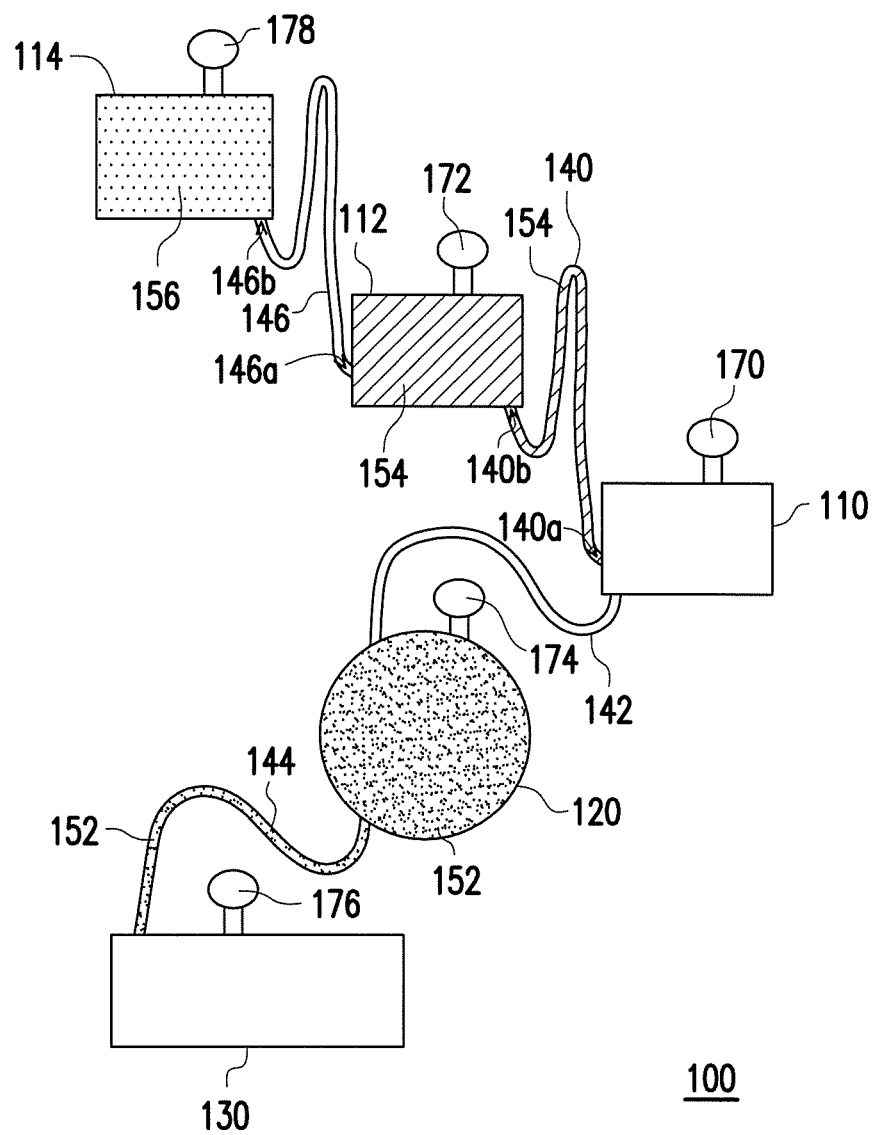

As FIG. 2B suggests, after rotation of the flow passage design 100, the specimen 152 enters the reaction tank 120, while the cleaning liquid 154 and the reagent 156 remain stored temporarily in the second temporary tank 112 and the third temporary tank 114 respectively. Specifically, after the specimen 152 enters the reaction tank 120, the first temporary tank 110 is empty at this time, that is, the outlet end 140a of the first microchannel 140 is not covered. Consequently, when the flow passage design 100 is kept standing for a period, a portion of the cleaning liquid 154 in the second temporary tank 112 enters the first microchannel 140 due to the capillary phenomenon. Meanwhile, a portion of the specimen 152 in the reaction tank 120 may also enter the third microchannel 144 due to the capillary phenomenon. In addition, since the inlet end 146b and the outlet end 146a of the fourth microchannel 146 are still covered by the reagent 156 and the cleaning liquid 154 respectively, the reagent 156 remains unable to enter the fourth microchannel 146 by the capillary phenomenon.

At this stage, since the first temporary tank 110 is empty, no liquid will be driven into the reaction tank 120 during the next rotation. Accordingly, the next rotation may serve to discharge the redundant waste liquid in the reaction tank 120 into the waste liquid tank 130.

Next, the flow passage design 100 is rotated again to apply a centrifugal force to the liquid in the microchannel. When the flow passage design 100 as shown in FIG. 2B is rotated, the cleaning liquid 154 in the first microchannel 140 and the specimen 152 in the third microchannel 144 are subjected to the centrifugal force and the siphon phenomenon is induced to respectively drive the cleaning liquid 154 in the second temporary tank 112 into the first temporary tank 110 and drive the specimen 152 in the reaction tank 120 into the waste liquid tank 130. In addition, since no liquid is in the fourth microchannel 146, the reagent 156 in the third temporary tank 114 is not driven when the flow passage design 100 is rotated.

Figure 2C:
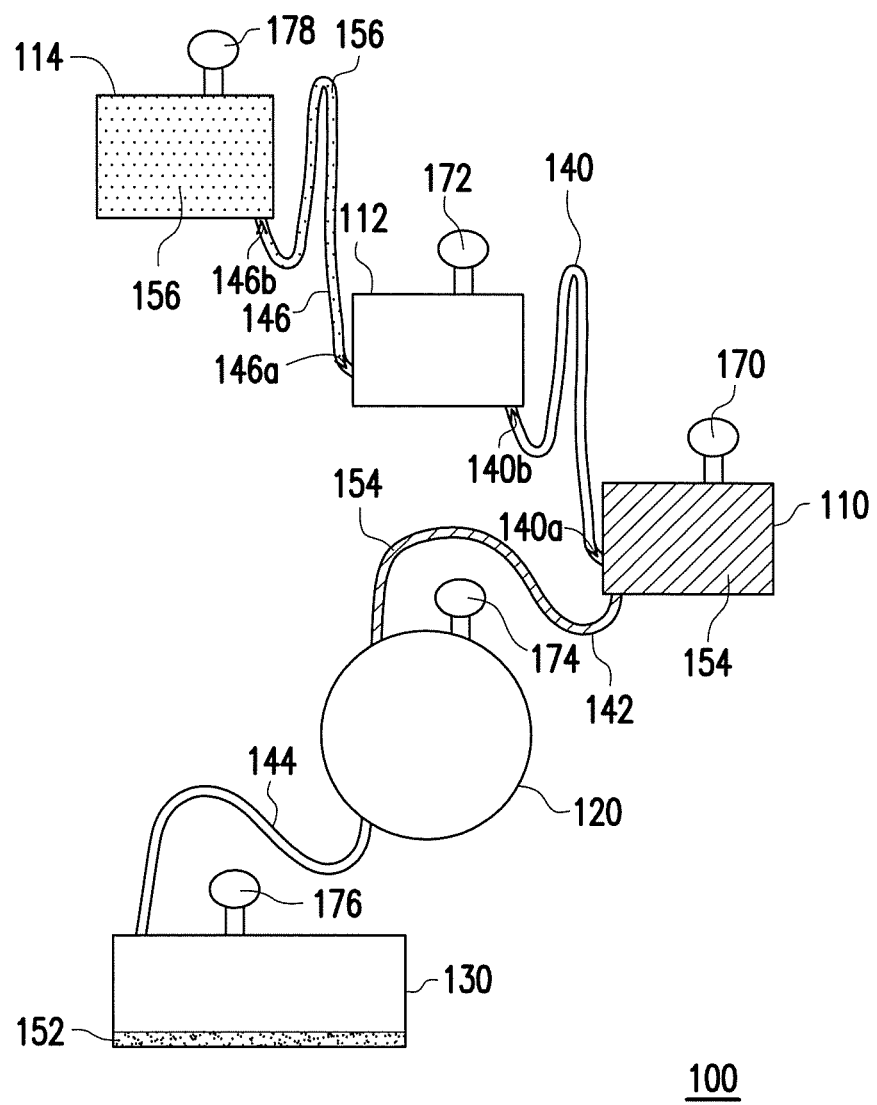

As FIG. 2C suggests, after rotation of the flow passage design 100, the specimen 152 enters the waste liquid tank 130, the cleaning liquid 154 enters the first temporary tank 110, and the reagent 156 remains stored temporarily in the third temporary tank 114. Specifically, after the cleaning liquid 154 enters the first temporary tank 110, the second temporary tank 112 is empty at this time, that is, the outlet end 146a of the fourth microchannel 146 is not covered. Consequently, when the flow passage design 100 is kept standing for a period, a portion of the reagent 156 in the third temporary tank 114 may enter the fourth microchannel 146 due to the capillary phenomenon. Meanwhile, a portion of the cleaning liquid 154 in the first temporary tank 110 may also enter the second microchannel 142 due to the capillary phenomenon.

Next, the flow passage design 110 is rotated again to apply a centrifugal force to the liquid in the microchannel. When the flow passage design 100 as shown in FIG. 2C is rotated, the cleaning liquid 154 in the second microchannel 142 and the reagent 156 in the fourth microchannel 146 are subjected to the centrifugal force and the siphon phenomenon is induced to respectively drive the cleaning liquid 154 in the first temporary tank 110 into the reaction tank 120 and drive the reagent 156 in the third temporary tank 114 into the second temporary tank 112.

Figure 2D:
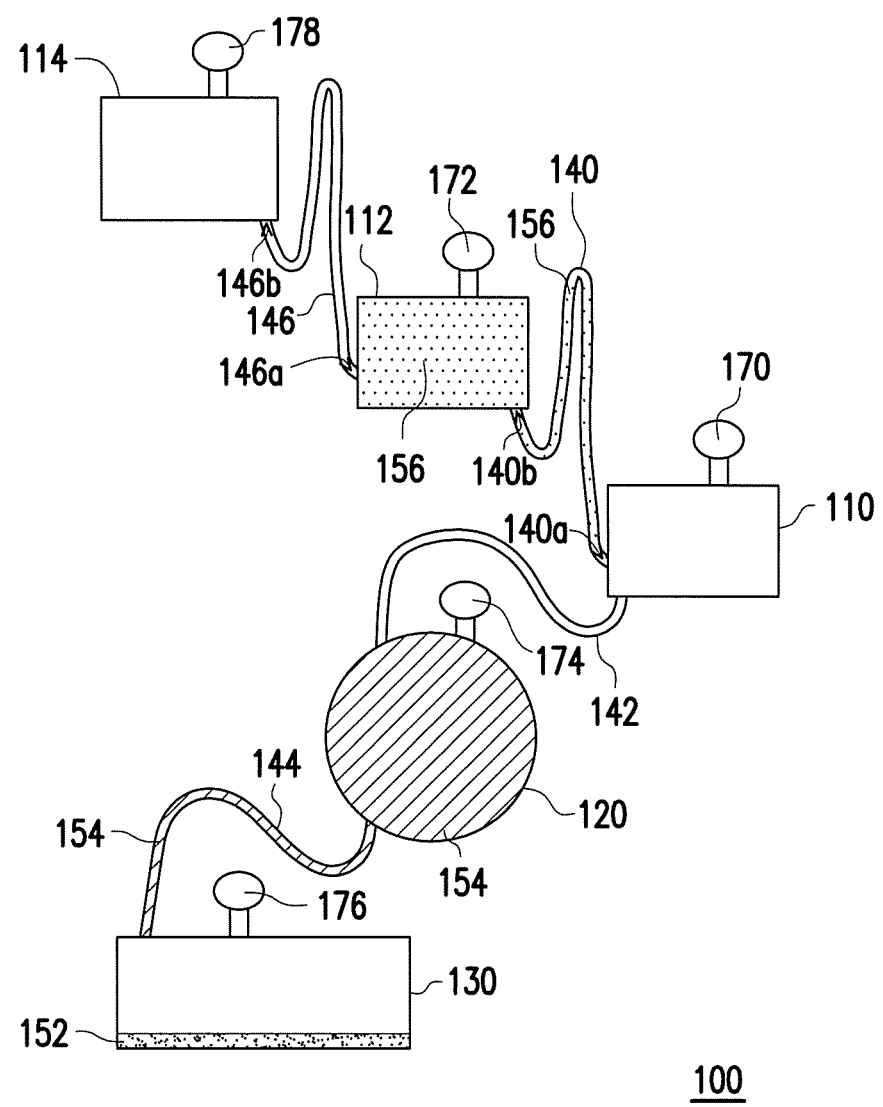

As FIG. 2D suggests, after rotation of the flow passage design 100, the cleaning liquid 154 enters the reaction tank 120, and the reagent 156 enters the second temporary tank 112. Specifically, after the cleaning liquid 154 enters the reaction tank 120, the first temporary tank 110 is empty at this time, that is, the outlet end 140a of the first microchannel 140 is not covered. Consequently, when the flow passage design 100 is kept standing for a period, a portion of the reagent 156 in the second temporary tank 112 may enter the first microchannel 140 due to the capillary phenomenon. Meanwhile, a portion of the cleaning liquid 154 in the reaction tank 120 may also enter the third microchannel 144 due to the capillary phenomenon.

Likewise, at the stage, since the first temporary tank 110 is empty, no liquid will be driven into the reaction tank 120 during the next rotation. Accordingly, the next rotation may serve to discharge the redundant waste liquid in the reaction tank 120 into the waste liquid tank 130.

Next, the flow passage design 100 is rotated again to apply a centrifugal force to the liquid in the microchannel. When the flow passage design 100 as shown in FIG. 2D is rotated, the cleaning liquid 154 in the third microchannel 144 and the reagent 156 in the first microchannel 140 are subjected to the centrifugal force and the siphon phenomenon is induced to respectively drive the cleaning liquid 154 in the reaction tank 120 into the waste liquid tank 130 and drive the reagent 156 in the second temporary tank 112 into the first temporary tank 110.

Figure 2E:
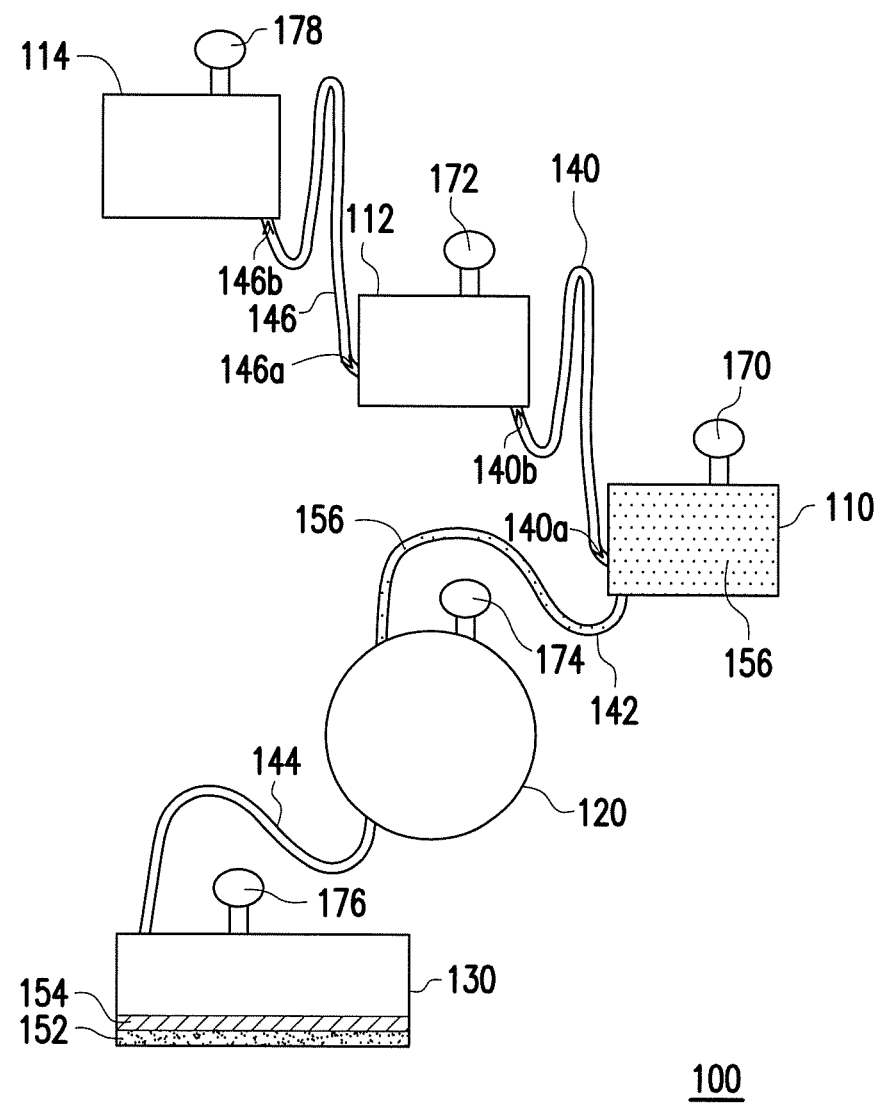

As FIG. 2E suggests, after rotation of the flow passage design 100, the cleaning liquid 154 enters the waste liquid tank 130, and the reagent 156 enters the first temporary tank 110. Likewise, when the flow passage design 100 is kept standing for a period, a portion of the reagent 156 in the first temporary tank 110 enters the second microchannel 142 due to the capillary phenomenon. Next, the flow passage design 100 is rotated again to apply a centrifugal force to the liquid in the microchannel.

Figure 2F:
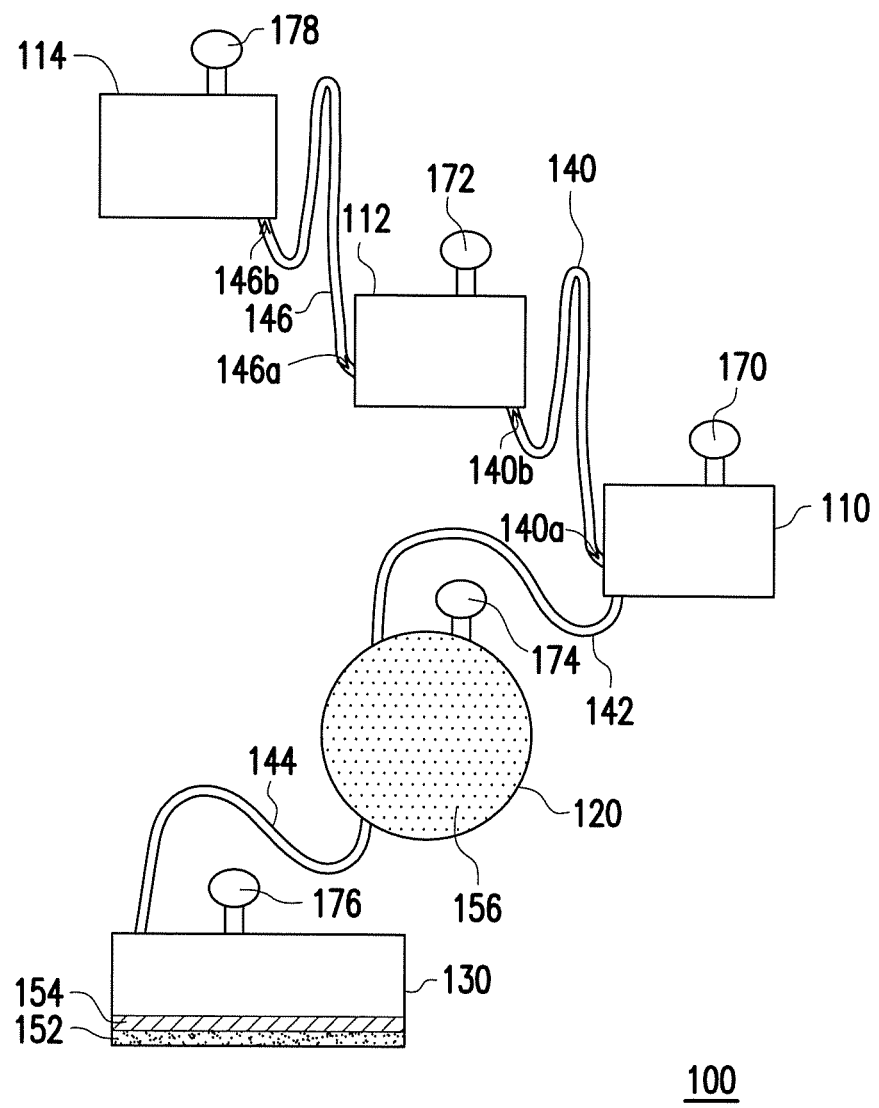

When the flow passage design 100 as shown in FIG. 2E is rotated, the reagent 156 in the second microchannel 142 are subjected to the centrifugal force and the siphon phenomenon is induced to drive the reagent 156 in the first temporary tank 110 to the reaction tank 120, as FIG. 2F suggest.

Through the above detection process, the specimen 152, the cleaning liquid 154 and the reagent 156 may be poured into the reaction tank 120 in sequence, and before the pouring of the specimen 152, the cleaning liquid 154 and the reagent 156 into the reaction tank 120, the redundant waste liquid in the reaction tank 120 is discharged into the waste liquid tank 130.

In view of the foregoing, in the flow passage design for multi-reaction biological detection and the detection method of the flow passage design for multi-reaction biological detection according to the embodiments of the invention, the inlet end and the outlet end of the microchannel disposed between the temporary tanks are covered by the liquids temporarily stored in the temporary tanks in the initial state to prevent the capillary phenomenon from being induced and consequently control the timing of the liquids pouring and leaving the reaction tank. Through the design, the flow passage design according to the embodiments of the invention is able to admit samples stepwise and significantly reduce the usage of the microchannel, reducing the volume and simplifying manufacturing.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:
1. A flow passage design for multi-reaction biological detection, suitable for detecting a first liquid, a second liquid and a third liquid, the flow passage design comprising:
the first liquid, the second liquid, and the third liquid are loaded respectively into a first temporary tank, a second temporary tank, and a third temporary tank;
a reaction tank and further comprising a reaction tank inlet and a reaction tank outlet;
the first temporary tank, configured to temporarily store the first liquid in an initial state and further comprising a first temporary tank inlet and a first temporary tank outlet;

the second temporary tank, configured to temporarily store the second liquid in the initial state and further comprising a second temporary tank inlet and a second temporary tank outlet;

the third temporary tank, configured to temporarily store the third liquid in the initial state and further comprising a third temporary tank outlet;

a first microchannel, located upstream of the first temporary tank and connecting to the first temporary tank and the second temporary tank, wherein no empty temporary tank is located between the first temporary tank, the second temporary tank and the third temporary tank;

a second microchannel, located downstream of the first temporary tank and connecting to the reaction tank and the first temporary tank; and a fourth microchannel, located upstream of the second temporary tank and directly connecting to the third temporary tank and the second temporary tank, wherein in the initial state, a portion of the first liquid enters the second microchannel, and wherein in the initial state, an outlet end of the first microchannel is covered by the first liquid, and an inlet end of the first microchannel is covered by the second liquid, wherein after the initial state, the flow passage design is rotated around a center of rotation for a first time, such that the first liquid leaves the first temporary tank through the second microchannel due to a centrifugal force and a siphon phenomenon, while the second liquid remains located in the second temporary tank, wherein a distance between the third temporary tank and the center of rotation is less than a distance between the second temporary tank and the center of rotation, and the distance between the second temporary tank and the center of rotation is less than a distance between the first temporary tank and the center of rotation.

2. The flow passage design according to claim 1, wherein in the initial state, the second liquid is unable to enter the first microchannel.

3. The flow passage design according to claim 1, wherein after being rotated for the first time, the flow passage design is kept standing for a period, such that a portion of the second liquid enters the first microchannel, the flow passage design is then rotated for a second time, such that the second liquid leaves the second temporary tank through the first microchannel and enters the first temporary tank.

4. The flow passage design according to claim 1, wherein the first liquid and the second liquid enter the reaction tank in sequence at different time points.

5. The flow passage design according to claim 1, wherein each of the first liquid and the second liquid is one of a specimen, a reagent and a cleaning liquid.

6. A detection method of a flow passage design for multi-reaction biological detection, wherein the flow passage design is suitable for detecting a first liquid, a second liquid and a third liquid and at least comprises a first temporary tank, a second temporary tank, a third temporary tank, a reaction tank, a first microchannel, a second microchannel and a forth microchannel, wherein the first liquid, the second liquid, and the third liquid are respectively loaded into a first temporary tank, a second temporary tank, and a third temporary tank, the first temporary tank comprises a first temporary tank inlet and a first temporary tank outlet, the second temporary tank comprises a second temporary tank inlet and a second temporary tank outlet, the third temporary tank comprises a third temporary tank outlet, the reaction tank comprises a reaction tank inlet and a reaction tank outlet, the first microchannel is located upstream of the first temporary tank and connects to the first temporary tank and the second temporary tank, the second microchannel is located downstream of the first temporary tank and connects to the reaction tank and the first temporary tank, the fourth microchannel is located upstream of the second temporary tank and directly connects to the third temporary tank and the second temporary tank, and no empty temporary tank is located between the first temporary tank, the second temporary tank and the third temporary tank, wherein the detection method comprising:

in an initial state, temporarily storing the first liquid in the first temporary tank, temporarily storing the second liquid in the second temporary tank, and temporarily storing the third liquid in the third temporary tank, wherein the first microchannel comprises an outlet end and an inlet end, respectively connecting to the first temporary tank and the second temporary tank, the outlet end of the first microchannel is covered by the first liquid, the inlet end of the first microchannel is covered by the second liquid, and a portion of the first liquid enters the second microchannel; and rotating the flow passage design around a center of rotation for a first time, such that the first liquid leaves the first temporary tank through the second microchannel due to a centrifugal force and a siphon phenomenon, while the second liquid remains located in the second temporary tank, wherein a distance between the third temporary tank and the center of rotation is less than a distance between the second temporary tank and the center of rotation, and the distance between the second temporary tank and the center of rotation is less than a distance between the first temporary tank and the center of rotation.

7. The detection method according to claim 6, wherein in the initial state, the second liquid is unable to enter the first microchannel.

8. The detection method according to claim 6, further comprising:

keeping the flow passage design standing for a period, such that a portion of the second liquid enters the first microchannel; and rotating the flow passage design for a second time, such that the second liquid leaves the second temporary tank through the first microchannel and enters the first temporary tank.

9. The detection method according to claim 6, wherein the first liquid and the second liquid enter the reaction tank at different time points.

* * * * *